United States Patent [19]
Holl et al.

[11] Patent Number: 5,866,151
[45] Date of Patent: Feb. 2, 1999

[54] ENCAPSULATED BIOCIDAL PREPARATION

[75] Inventors: Richard J. Holl; David W. Mason; Alan H. Dean, all of Birmingham, Ala.

[73] Assignee: Southern Research Institute, Birmingham, Ala.

[21] Appl. No.: 630,363

[22] Filed: Apr. 10, 1996

[51] Int. Cl.$^6$ .................................................. A01N 25/34
[52] U.S. Cl. ...................... 424/405; 424/408; 424/409; 424/419
[58] Field of Search .................................. 424/405, 409, 424/499, 408, 419; 514/365

[56] References Cited

U.S. PATENT DOCUMENTS

| | | | |
|---|---|---|---|
| 3,983,252 | 9/1976 | Buchalter | 424/333 |
| 4,122,192 | 10/1978 | Fellows | 424/333 |
| 4,362,241 | 12/1982 | Williams | 206/210 |
| 4,552,591 | 11/1985 | Millar | 106/18.33 |
| 4,677,003 | 6/1987 | Redlich et al. | 427/373 |
| 4,722,865 | 2/1988 | Huizer | 428/407 |
| 4,908,262 | 3/1990 | Nelson | 428/283 |
| 4,985,064 | 1/1991 | Redlich et al. | 71/90 |
| 5,061,106 | 10/1991 | Kent | 401/268 |
| 5,063,248 | 11/1991 | Conlan et al. | 514/665 |
| 5,158,972 | 10/1992 | Whitekettle et al. | 514/471 |
| 5,164,096 | 11/1992 | Nunn | 210/754 |
| 5,480,643 | 1/1996 | Donovan et al. | 424/409 |

FOREIGN PATENT DOCUMENTS

93/02668   2/1993   WIPO.

*Primary Examiner*—Thurman K. Page
*Assistant Examiner*—Kathryne E. Shelborne
*Attorney, Agent, or Firm*—Needle & Rosenberg, P.C.

[57] ABSTRACT

A composition, comprising an agent, a carrier admixed with the agent to form a mixture, and a film-forming polymer coating around the mixture which is insoluble in a selected solvent. A biocidal composition, comprising a biocide, such as an aldehyde, a carrier admixed with the aldehyde to form a mixture, and a film-forming polymer coating around the mixture which is insoluble in a selected solvent. The composition of the invention further comprising an acidifying agent admixed with the aldehyde. The composition of the invention and an activator. An article of manufacture, comprising the composition of the invention contained inside a fluid-permeable mesh bag. A method of making a biocidal composition, comprising admixing a carrier with an aldehyde to form a mixture, and coating the mixture with a film-forming polymer coating which is insoluble in a selected solvent. A method of making a biocidal article of manufacture, comprising enclosing within a fluid-permeable mesh bag the biocidal composition of the invention and an activator. A method of making a biocidal composition, comprising contacting the biocidal composition of the invention with the selected solvent and adding an activator to the composition in the solvent.

17 Claims, 1 Drawing Sheet

ENCAPSULATED BIOCIDAL PREPARATION

BACKGROUND OF THE INVENTION

1. Field of the Invention

The invention relates to an encapsulated agent, preferably a biocidal preparation. In particular, the preparations of the invention provide a means for safely transporting a biocide such as an aldehyde, preferably glutaraldehyde, to an end-use destination and for preserving the biocidal activity of the biocidal agent until it is ready to be used at the destination.

2. Background Art

Aldehydes, and especially dialdehydes, can be potent biocidal compounds. One particular dialdehyde, glutaraldehyde, is a strong disinfectant. Glutaraldehyde is a 5-carbon molecule and possesses two aldehyde groups (i.e., a dialdehyde). Glutaraldehyde is the most potent disinfectant of the aldehyde class. It is available commercially as a 2 weight ("wt") % aqueous solution (Johnson & Johnson Co.) at pH 4.0. When made alkaline, pH 7.5–8.5, the 2 wt % glutaraldehyde is a rapid acting disinfectant. It is classified as a high-level germicide and is capable of producing sterility, i.e., eradicating all living bacteria, microorganisms and spores. Most bacteria are killed in less than 1 minute. *Tubercie bacillus* and viruses are killed in less than 10 minutes. And, bacterial spores are killed in less than 3 hours.

The 2 wt % glutaraldehyde solution has high stability when kept acidic. However, to be germicidal, the glutaraldehyde solution must be made alkaline. The alkaline glutaraldehyde solution is only stable for about 2 to 4 weeks. Under alkaline conditions, glutaraldehyde slowly polymerizes resulting in decreased germicidal activity.

The primary application for glutaraldehyde is as a cold disinfectant or sterilant or heat-sensitive medical and dental instruments. For disinfection, a 20 minute immersion in a 2 wt % glutaraldehyde alkaline solution is recommended. For sterilization, a 10–12 hour immersion is recommended. After immersion in the glutaraldehyde for the recommended time, the instruments are rinsed with sterile water.

Because of its strength as a disinfectant, care must be exercised when handling glutaraldehyde solutions, including the use of gloves and aprons when handling glutaraldehyde solutions. In addition, adequate ventilation should be provided when handling glutaraldehyde solutions. Glutaraldehyde solutions have been reported to produce contact dermatitis, eye irritation, nausea, headache, rashes, and asthmatic reactions.

U.S. Pat. No. 4,122,192 to Fellows discloses a glutaraldehyde containing disinfectant preparation. That preparation consists of glutaraldehyde (or a saturated dialdehyde of 2 to 6 carbons) absorbed and/or adsorbed on a carrier material. In some cases an alkalinating, activating agent is also included, which can be encapsulated in a water-soluble polymer. The '192 preparations suffer from several drawbacks. First, the glutaraldehyde itself is not isolated from human contact in the unused preparation. Second, the carrier material may freely enter the solution upon use of the preparation. Such entry into the cleaning solution of carrier material is undesirable. Furthermore, depending upon the original pH of the glutaraldehyde solution, some inactivation of the glutaraldehyde may occur in situ.

Because of its toxicity, glutaraldehyde is sold to the end-user as the 2 wt % glutaraldehyde aqueous solution. However, even the 2 wt % glutaraldehyde solution has toxicity and handling problems. A method of making aldehydes, particularly glutaraldehyde, safer to handle which lessens the toxicity and handling problems to the end-user is therefore highly desirable. Such a method would greatly increase the appeal of aldehydes, such as glutaraldehyde, as cold sterilants. In addition, there exists a need for a cost-effective mode of handling and delivering aldehydes. Finally, the method must provide a stable aldehyde or biocidal solution that can be readily and easily activated.

SUMMARY OF THE INVENTION

The present invention provides a composition, comprising an agent, a carrier admixed with the agent to form a mixture, and a film-forming polymer coating around the mixture which is insoluble in a selected solvent.

The present invention also provides a biocidal composition, comprising an aldehyde, a carrier admixed with the aldehyde to form a mixture, and a film-forming polymer coating around the mixture which is insoluble in a selected solvent.

In yet another embodiment, the present invention provides a biocidal composition further comprising an activator.

In a further embodiment, the present invention provides an article of manufacture, comprising the composition of the invention contained inside a fluid-permeable mesh bag.

In addition, the present invention provides a method of making a biocidal composition, comprising admixing a carrier with an aldehyde to form a mixture and coating the mixture with a film-forming polymer coating which is insoluble in a selected solvent.

In yet another embodiment, the present invention provides a method of making a biocidal article of manufacture, comprising enclosing within a fluid-permeable mesh bag the biocidal composition of the invention and an activator.

In a further embodiment, the present invention provides a method of making a biocidal composition, comprising contacting the biocidal composition of the invention with the selected solvent and adding an activator to the composition in the solvent.

In yet another embodiment, the present invention provides a composition, comprising a compound which is liquid at a preselected processing temperature, a carrier admixed with the compound to form a mixture, and a film-forming polymer coating around the mixture which is insoluble in a selected solvent.

The present invention also provides a biocidal composition, comprising a biocidal compound which is liquid at a preselected processing temperature, a carrier admixed with the compound to form a mixture, and a film-forming polymer coating around the mixture which is insoluble in a selected solvent.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Figure 1:
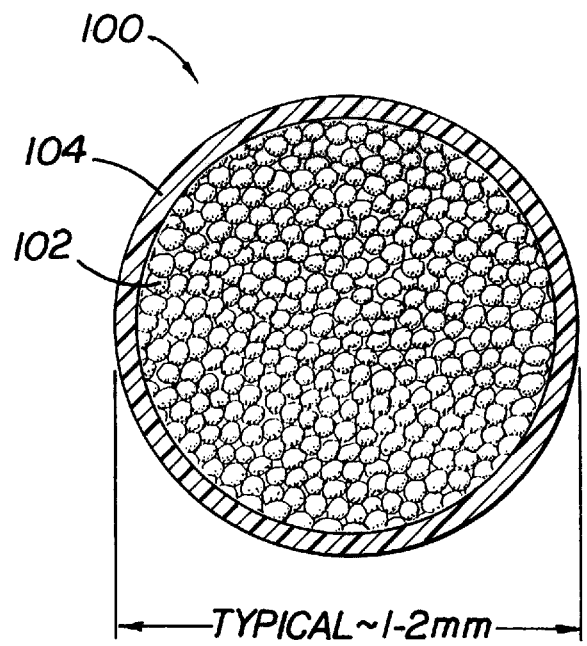
FIG. 1 shows, schematically, a cross-section of a coated, aldehyde-loaded bead of one embodiment of the invention.

The present invention may be understood more readily by reference to the following detailed description of preferred embodiments of the invention and to the Figures.

Before the present devices and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

Throughout this application, various publications are referenced. The disclosures of these publications in their entireties are hereby incorporated by reference into this application in order to more fully describe the state of the art to which this invention pertains.

The present invention provides a composition, comprising an agent, a carrier admixed with the agent to form a mixture, and a film-forming polymer coating around the mixture which is insoluble in a selected solvent. In a particular embodiment, the selected solvent is water and the film-forming polymer is a water-insoluble polymer.

The present invention provides a biocidal composition, where the agent is a biocide which can be, but does not necessarily have to be, an aldehyde, a carrier admixed with the biocide or aldehyde to form a mixture, and a film-forming polymer coating around the mixture which is insoluble in a selected solvent. In a further preferred embodiment, the present invention further comprises an acidifying agent admixed with the biocide or aldehyde. More preferably, if the biocide is an aldehyde, then it is a dialdehyde such as glutaraldehyde.

In an alternative embodiment, the present invention provides a biocidal composition further comprising an activator.

In another embodiment, the carrier is an adsorbent. More preferably the carrier is a carbon, cellulosic compound, chitin, cyclodextran, acid-treated clay, activated alumina, magnesium silicate, silica gel, molecular sieves, fuller's earth, or a mixture thereof. A particularly preferable carrier is microcrystalline cellulose.

The present invention further provides the biocidal composition of the invention wherein the selected solvent is water and the film-forming polymer is a water-insoluble polymer.

Preferably, the biocidal composition of the invention is formulated such that the water-insoluble, film-forming polymer is a poly(acrylic), poly(methacrylics), poly(vinyl ether), poly(vinyl ester), polystyrene, polyurethane, polyoxide, polycarbonate, cellulose ester, cellulose ether, polyester, or a mixture thereof. More preferably, the water-insoluble, film-forming polymer is cellulose acetate, ethyl cellulose, or a mixture thereof.

In an alternative embodiment, the activator is an alkalinating agent. More preferably, the alkalinating agent is sodium bicarbonate, borax, disodium hydrogen phosphate, or a mixture thereof. Even more preferably, the alkalinating agent is sodium bicarbonate.

In another embodiment, the acidifying agent is acetic acid, hydrochloric acid, or phosphoric acid. More preferably, the acidifying agent is acetic acid.

In yet another embodiment, the present invention provides a biocidal composition wherein the aldehyde comprises from 10 to 50 weight percent of the composition, the carrier comprises from 10 to 50 weight percent of the composition, the film-forming polymer comprises from 1 to 10 weight percent of the composition, and the activator comprises from 1 to 10 weight percent of the composition. More preferably, the aldehyde comprises from 40 to 50 weight percent of the composition, the carrier comprises from 40 to 50 weight percent of the composition, the film-forming polymer comprises from 1 to 5 weight percent of the composition, and the activator comprises from 1 to 5 weight percent of the composition.

In yet another embodiment, the present invention provides an article of manufacture, comprising the composition of the invention contained inside a fluid-permeable mesh bag. In a preferred embodiment, the mesh bag is comprised of a plastic. More preferably, the plastic is a nylon, polyester, polyethylene, polypropylene, fluorocarbon, or a mixture thereof. Even more preferably, the plastic is nylon.

Furthermore, the present invention provides a method of making a biocidal composition, comprising admixing a carrier with an aldehyde to form a mixture and coating the mixture with a film-forming polymer coating which is insoluble in a selected solvent. More preferably, the aldehyde is a dialdehyde, such as glutaraldehyde.

In yet another embodiment, the method further comprises contacting the aldehyde with an acidifying agent before the admixing step.

The present invention also provides a method of making a biocidal article of manufacture, comprising enclosing within a fluid-permeable mesh bag the biocidal composition of the invention and an activator.

In addition, the present invention provides a method of making a biocidal composition, comprising contacting the biocidal composition with the selected solvent and adding an activator to the composition in the solvent.

A further embodiment provides a method of using a biocidal composition, comprising contacting the biocidal composition of the invention with the selected solvent.

In a preferable embodiment of the above methods, the carrier is an adsorbent. More preferably, the carrier is a carbon, cellulosic, chitin, cyclodextran, acid-treated clay, activated alumina, magnesium silicate, silica gel, molecular sieve, fuller's earth, or a mixture thereof. In a particularly preferable embodiment, the carrier is microcrystalline cellulose.

Furthermore, the present invention provides the above method wherein the film-forming polymer is a water-insoluble polymer. More preferably, the water-insoluble polymer is a poly(acrylic), poly(methacrylic), poly(vinyl ether), poly(vinyl ester), polystyrene, polyurethane, polyoxide, polycarbonate, cellulose ester, cellulose ether, polyester, or a mixture thereof. Even more preferably, the water-insoluble polymer is cellulose acetate, ethyl cellulose, or a mixture thereof.

In alternative embodiments, the activator is an alkalinating agent. More preferably, the alkalinating agent is sodium bicarbonate, borax, disodium hydrogen phosphate, or a mixture thereof. Even more preferably, the alkalinating agent is sodium bicarbonate.

In yet another embodiment, the acidifying agent is acetic acid, hydrochloric acid, phosphoric acid, or a mixture thereof. More preferably, the acidifying agent is acetic acid.

In another preferable embodiment of the methods of the present invention, the aldehyde comprises from 10 to 50 weight percent of the composition, the carrier comprises from 10 to 50 weight percent of the composition, the film-forming polymer comprises from 1 to 10 weight percent of the composition, and the activator comprises from 1 to 10 weight percent of the composition. More preferably, the aldehyde comprises from 40 to 50 weight percent of the composition, the carrier comprises from 40 to 50 weight percent of the composition, the film-forming polymer comprises from 1 to 5 weight percent of the composition, and the activator comprises from 1 to 5 weight percent of the composition.

In alternate embodiments of the methods of the present invention, the mesh bag is comprised of a plastic. More preferably, the plastic is a nylon, polyester, polyethylene, polypropylene, fluorocarbon, or a mixture thereof. Even more preferably, the plastic is nylon.

In yet another embodiment of the methods of the present invention, the film-forming polymer coating further comprises a solvent-soluble film-forming polymer admixed with the solvent-insoluble film-forming polymer. More preferably, the film-forming polymer coating further comprises a water-soluble film-forming polymer admixed with the water-insoluble film-forming polymer. Even more preferably, the water-soluble polymer is polyvinylpyrrolidone.

The present invention is useful for delivering concentrated, highly corrosive materials or other agents. Such materials include, but are not limited to, organic liquids with suitable boiling points and vapor pressures. A preferred material is a liquid biocidal agent or biocide. Preferably, the biocidal agent is an acid-preserved, base-activated biocidal agent. More preferably, the acid-preserved, base-activated biocidal agent is an aldehyde. Suitable aldehydes include, but are not limited to, formalin (34–38% formaldehyde in water solution), acetaldehyde, propionaldehyde, butyraldehyde, pentanal, hexanal, heptanal, octanal, nonanal, decanal, where the aldehyde may be branched or unbranched. More preferably, the aldehyde class biocidal agent is a dialdehyde. Suitable dialdehydes include, but are not limited to the dialdehyde forms of the above-mentioned aldehydes. The presently described methods and compositions are applicable to other biocidals such as other dials, malonaldehyde, succinaldehyde, adipaldehyde, glyoxal, hexamethylenetetramine, formalin, isothiazalone(2-N-octal-4-isothiazolin-3-one), acrolein, perchloric acid and diethyl toluamide. Furthermore, trialdehydes and higher aldehydes are also suitable for use in the biocidal preparations of the present invention, although stabilizing additives may be added to prevent autopolymerization.

Thus, the present invention will work with any agent or compound that can be absorbed into a suitable carrier, e.g. microcrystalline cellulose, and is liquid at processing temperature. The compound or agent can be toxic and can have a point of application which is separated from the point of manufacture. Finally, the compound is preferably dissolvable or otherwise dispersible in the chosen solvent, such as water, in order to form the preferred mixture.

For example, the agent can be glutaraldehyde. The official chemical name of glutaraldehyde is 1,5-pentanedial. Glutaraldehyde is a liquid at room temperature, its melting point is −6° C., and its boiling point is 187°–9° C. with decomposition. Because glutaraldehyde tends to self-polymerize, glutaraldehyde is typically available as a solution in acidified water. Acidification of the glutaraldehyde solution inhibits self-polymerization. The highest concentration of glutaraldehyde commercially available is a 70 wt % solution.

The amount of aldehyde, such as glutaraldehyde, to be incorporated in the preparations of the present invention is preferably 1–99 wt %, and more preferably 10–60, and even more preferably 45–55 wt %. Bulk quantities of aldehydes, such as glutaraldehyde, are typically supplied as a 50 wt % aqueous solution. This limits the amount of glutaraldehyde that can be incorporated into the adsorbent. Any concentration of glutaraldehyde in water (or another suitable solvent) can be used as the source of glutaraldehyde for the preparation. However, using higher glutaraldehyde concentration solutions in making the preparation results in higher final glutaraldehyde concentrations in the preparation.

In a preferred embodiment, the stability of the glutaraldehyde incorporated into the preparations of the current invention can be increased by incorporating a suitable acidifying agent into the glutaraldehyde solution, preferably before making the preparations. Preferable acidifying agents include, but are not limited to, acetic acid, hydrochloric acid, phosphoric acid, or other acidifying agents capable of lowering the glutaraldehyde solution to pH 4.0.

Preferable carriers for glutaraldehyde in the preparations of the present invention are adsorbents such as a carbon, a cellulosic compound, a chitin, a cyclodextran, an acid-treated clay, an activated alumina, a magnesium silicate, silica gel, a molecular sieve, or fuller's earth. The adsorbents can be use alone or in combinations of two or more of the listed adsorbents without altering the basic characteristics of the present invention. A preferable adsorbent is microcrystalline cellulose (Avicel PH-101, FMC Corp., Philadelphia, Pa.).

The amount of adsorbent incorporated in the preparations varies depending upon the type of adsorbent used and the glutaraldehyde loading capability of the adsorbent. In general, however, a preferable range is 1–99 wt % of adsorbent, more preferably, 40 to 90 wt %, and with a particularly preferable range being 45–55 wt %.

In the preparations of the present invention, the adsorbent aldehyde mixture is formed into a convenient shape, such as a bead. To maintain the structural integrity of the beads after immersion in water, the beads are coated with a thin layer of film-forming polymer. Film-forming polymers that are insoluble in the solvent which the beads will be placed in are preferable for use as the coating of the adsorbent beads. If the solvent is water, then water-insoluble film-forming polymers may be used in one embodiment. The water-insoluble polymer must, however, be permeable to the biocidal agent, such as an aldehyde like glutaraldehyde. Permeability can be accomplished via a concentration gradient between the aldehyde inside the polymer and the aldehyde outside the polymer or via the formation of pores by the dissolution of a solvent-soluble polymer which is mixed in with the solvent-insoluble polymer.

It should be noted that, as used herein, the terms "soluble" and "insoluble" do not refer to any absolutes. In fact, insolubility is only required to the extent that the biocidal agent is maintained within the beads in a stable state for a desired period of time, i.e., a desired shelf-life. The presently used term "insoluble" thus does not require absolute insolubility in the chosen solvent. Similarly, the term "soluble" does not require complete or rapid dissolution of a material. Rather, a "soluble" material must dissolve for the duration and extent necessary for the presently described methods and compositions to sustain the recited utilities.

Preferable water-insoluble polymers are poly(acrylics), poly(methacrylics), poly(vinyl ethers), poly(vinyl esters), polystyrenes, polyurethanes, polyoxides, polycarbonates, cellulose esters, cellulose ethers, polyesters or mixtures of two or more thereof. More preferable polymers include cellulose acetate and ethyl cellulose. Polyvinylpyrrolidine ("PVP"), which is water-soluble, can be added to the water-insoluble polymer so that upon contacting the beads with water, pores in the polymer are formed to expedite permeation of aldehyde therethrough. This invention is not limited to water-insoluble polymers and water as a solvent. Instead, many other solvents could be used, so long as a solvent-insoluble polymer was used and the polymer was permeable to glutaraldehyde.

The preparations of the present invention can be prepared according to conventional methods of contacting the glutaraldehyde with the adsorbent. An acidifying agent, such as an acid, may optionally be added to the aldehyde prior to or after mixing with the adsorbent to increase the aldehyde's shelf-life or stability. The processing step can be performed in a planetary mixer or a conventional tumbling mixer such as a double-cone mixer or a twin-shell blender. Depending on the concentration of bulk glutaraldehyde solution, water is added to the glutaraldehyde-loaded adsorbent to form an extrudable paste. The glutaraldehyde-loaded adsorbent paste is extruded to form a cylindrical rod. Various extruders can be used to form the cylindrical rod. The extruded glutaraldehyde-loaded adsorbent rods are then placed in a spheronizer (Model R, Fluid Bed Rotor, Glatt Air Technologies, Inc., Ramsey, N.J.). The extruded glutaraldehyde-loaded adsorbent rods must be kept moist and not be allowed to dry. Otherwise, the spheronizer will not be able to form suitable beads from the rod.

The spheronizer processes the rods into spherical pellets. The water content of the extruded glutaraldehyde-loaded rods is controlled so that the extruded rods can be easily broken by the action of the spheronizer. The spheronizer operates by imparting shear energy to the rods. Shear energy is applied to the rods using a rotating disc situated axially in a stationary cylinder. By applying shear energy, the rods are broken down into cylinders with lengths approximately equal to their diameters. This condition represents a low-energy state for the rods undergoing shear in the spheronizer. Once cylinders of these dimensions are formed, the tumbling action of the cylinders in the spheronizer rounds the edges of the cylinders and forms spheres.

In reference to FIG. 1, once the glutaraldehyde-loaded adsorbent spheres 102 are made, they are coated with the film-forming polymer 104. The polymer 104 can be applied to the adsorbent/glutaraldehyde spheres 102 by various methods known to those of ordinary skill in the art. In one embodiment, the water-insoluble polymer 104 is applied as a solution in acetone/water to the glutaraldehyde-loaded adsorbent spheres 102 using a spray nozzle located inside the spheronizer. By forcing air under pressure through the spheres in the spheronizer, the polymer solution coating 104 the spheres 102 can dry and form a polymer film 104 around the spheres. As a result, glutaraldehyde-loaded adsorbent, polymer coated beads 100 are both made and coated with the polymer 104 inside the spheronizer. Other methods of making and coating beads are known to skilled artisans.

Figure 2:
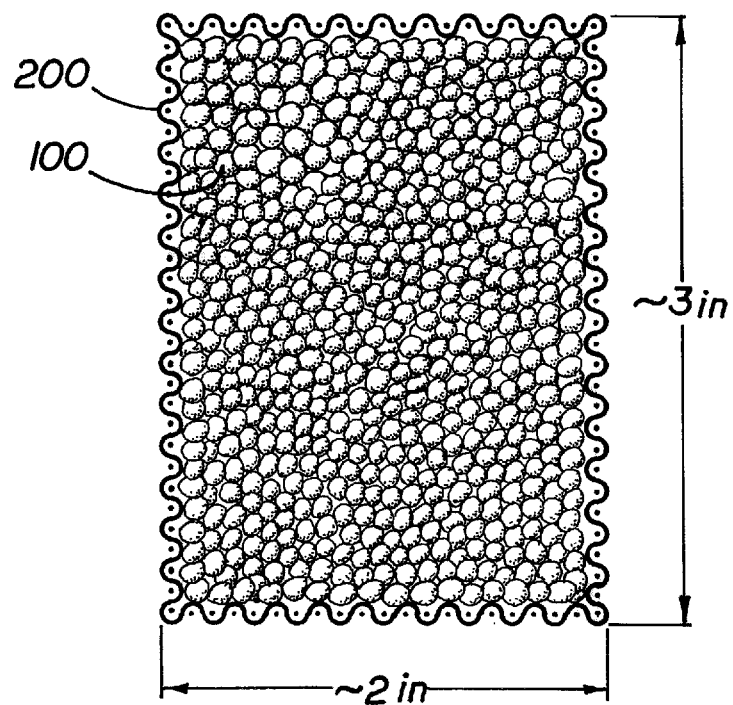
FIG. 2 shows the coated, aldehyde-loaded beads in a plastic mesh bag.

In reference to FIG. 2, after glutaraldehyde-loaded adsorbent beads 100 are made and coated with water-insoluble polymer 104, they can, in one embodiment, be packaged into mesh bags 200, preferably a plastic mesh bag. Incorporating the coated glutaraldehyde-loaded adsorbent beads 100 into the mesh bags 200 provides a convenient method of dispensing the proper amount of beads 100 into a given amount of solvent to prepare a 2 wt % glutaraldehyde solution. The size and physical characteristics of the mesh bags 200 can be adjusted according to the size of the beads 100 and the amount of beads 100 necessary. For instance, a large mesh bag 200 would be provided to deliver 20 kg. of acrolein. Therefore, the scale of the mesh bags 200 is specifically not intended to be limited.

An activator can also be included in the plastic mesh bags 200 to provide a convenient method of activating the glutaraldehyde solution. Preferable activators are sodium bicarbonate, borax, disodium hydrogen phosphate and other compounds capable of alkalinating the glutaraldehyde solution. The most preferable activating agent is sodium bicarbonate. The amount of activator can be adjusted by the skilled artisan, without undue experimentation, to achieve a preferred, final solution pH of 7.5 to 8.5. A mixture of activators can be used.

Other ingredients can be added to the preparations of the present invention to increase their market appeal without altering the basic and novel characteristics of the present invention. For instance, dyes, fragrances and pH indicators can be used.

The glutaraldehyde preparation of the present invention enables the delivery of concentrated glutaraldehyde to end-users for use as a cold sterilant, ie., one that does not require heat for sterilization efficacy. The preparation of the present invention has significant advantages over the current glutaraldehyde products. These advantages include, but are not limited to, lower transportation costs because of the concentrated nature of the glutaraldehyde used, increased safety because the glutaraldehyde is in the form of a solid, rather than a liquid, and decreased handling difficulties because the prepackaged amounts of dry, glutaraldehyde-loaded beads 100 are presented in fluid permeable bags such as mesh bags 200.

It must be emphasized that while the examples herein often describe the delivery of glutaraldehyde, the present invention is not limited in its scope to that compound alone. Instead, the invention provides a general delivery system wherein an agent to be delivered is encapsulated and delivered as described. The agent can, alternatively, be a biocidal agent.

The preferred embodiments of the above-described preparations are set forth in the following examples. Similar structures have been referenced with the same numerals throughout the Figures referred to in the Examples. Other features of the invention will become apparent from the following examples, which are for illustrative purposes only and are not intended as a limitation upon the present invention.

EXAMPLES

Example 1

Fifty (50) grams of microcrystalline cellulose (Avicel PH-101, FMC Corp., Philadelphia, Pa.) was placed in planetary mixer (KitchenAid Model K5SS, KitchenAid, Inc., St. Joseph, Mich.) with a large mixing blade. The mixer was activated at slow speed to slowly move the microcrystalline cellulose. 64 mL of 50 wt % glutaraldehyde in water solution (Ucarcide 250 Antimicrobial, Union Carbide Corp., Danbury, Conn.) was added slowly to the cellulose. Mixing was continued until homogenous paste was obtained.

The paste was then collected and transferred to an extruder (Micro-Granulator, Model KAR-75, Luwa Corp., Charlotte, N.C.) with an appropriate screen to produce 1- to 2-mm cylindrical rods. The extruder was operated to produce such cylindrical rods.

The extruded rods were transferred to a spheronizer. The present example used a spheronizer constructed from an 8" metal plate having a 90° cross-hatch with parallel grooves with dimensions approximately 1-mm deep by 1-mm wide and placed on 3-mm centers. The plate was situated in an 8" inside diameter metal cylinder. The clearance between the plate and cylinder was small. The metal plate was coaxially attached to a rod which, in turn, was connected to a variable-speed motor.

The extruded paste was spheronized at 1200 rpm for about 1 minute. This spheronization produced spheres with diameters of from about 1- to 2-mm. While being processed in the spheronizer, the mass of spheres was lightly dusted with microcrystalline cellulose to prevent agglomeration in the spheronizer. In the present example, approximately 5 g. of microcrystalline cellulose was used during spheronization. A skilled artisan could readily adjust this amount as necessary.

Once satisfactory beads were produced, they were coated with a thin film of cellulose acetate. Cellulose acetate solution was first prepared by dissolving approximately 45 g. of cellulose acetate (Cellulose acetate, Grade CA 398-10, FMC Corporation, Philadelphia, Pa.) in 2 l. of a 3 wt % water in acetone solution. This produced a cellulose acetate concentration of 2.3 wt %.

While the spheres were still in the spheronizer, the spinning speed was reduced to about 700 rpm. Compressed air was fed through an inlet port in the spheronizer cylinder wall located under the spheronizer plate. By supplying compressed air under the spheronizer plate, the beads were effectively fluidized. In the present example, the air was supplied to the spheronizer at 65 psig.

An ultrasonic spray nozzle (MicroSpray Nozzle, Model 8700-60MS, Sono-Tek Corp., Poughkeepsie, N.Y.) was used to spray the cellulose acetate solution onto the spheres. The ultrasonic spray nozzle was situated inside the spheronizer cylinder at a distance of about 2.5 cm from the mass of beads. A syringe pump (Infusion/Withdrawal Pump, Model 944, Harvard Apparatus, Millis, Mass.) was used to pump the cellulose acetate solution to the ultrasonic spray nozzle. The cellulose acetate solution was pumped at 1.9 mL/minute flow rate. A total of about 85 mL of cellulose acetate solution was sprayed onto the 50 g. of spheres. This corresponds, approximately, to 2 g. of cellulose acetate deposited onto the spheres as an approximately 2.5 $\mu$m film.

After the spheres were coated (resulting in coated beads 100), they were removed from the spheronizer and packaged in square-weave, Nylon mesh bags with 500 $\mu$m mesh openings (Spectra/Mesh Nylon, Spectrum, Houston, Tex.). The bags were prepared by heat-sealing together three sides of two 2" by 3" sheets of Nylon mesh. The bag was filled with about 50 g. of finished glutaraldehyde beads and the fourth side of the bag was then heat-sealed. The filled bag contained enough glutaraldehyde-loaded beads to prepare 1 l. of 2 wt % glutaraldehyde solution.

Upon use, the bag is submersed in about 1 L of water at room temperature. A concentration gradient across the water-insoluble polymer allows the glutaraldehyde to permeate out of the beads and out of the mesh bag. The water-insoluble polymer traps the carrier within. Furthermore, the bag prevents the water-insoluble polymer from entering the solution. Thus, there is little or no contamination of the glutaraldehyde solution with carrier or polymer. After the solution is formed, the mesh bag is simply removed from the solution and discarded.

Example 2

The preparation is the same as Example 1, except that an acidifying agent is added. The acidifying agent is added to the glutaraldehyde solution before contacting with the microcrystalline cellulose. The pH of the commercial Ucarcide™ 250 (2 wt % glutaraldehyde) is from about 3.1 to 4.5.

Example 3

The preparation is also the same as Example 1, except that a water-soluble polymer was added to the film-forming polymer. Polyvinylpyrrolidone ("PVP") was added to the cellulose acetate solution before spraying. Such addition forms a colloidal suspension of PVP in the cellulose acetate solutions. In this example, equal amounts of PVP and cellulose acetate were used. 45 g. of cellulose acetate was dissolved in 2 l. of 3 a 3 wt. % water in acetone solution. After the cellulose acetate was dissolved, 45 g. of PVP (PVP-10, Sigma Chemical Co., St. Louis, Mo. 63178) was added and the resulting suspension was agitated until a uniform consistency was obtained. When using such a nonhomogeneous film-forming polymer, contacting the glutaraldehyde encapsulated in this mixed coating with water only permitted the water-soluble polymer to be dissolved. This permitted the encapsulated glutaraldehyde to enter the solution directly. Depending upon the amount and nature of the water-soluble polymer and the properties of the carrier material, the carrier material could be trapped inside the water-insoluble sphere.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. An article of manufacture, comprising: a composition comprising a biocidal agent, wherein the agent is an aldehyde; a carrier admixed with the agent to form a mixture; an activator, and a film-forming polymer coating around the mixture which is insoluble in a selected solvent contained inside a fluid-permeable mesh bag.

2. The article of claim 1, wherein the mesh bag is comprised of a plastic.

3. The article of claim 2, wherein the plastic is a nylon, polyester, polyethylene, polypropylene, fluorocarbon, or a mixture thereof.

4. The article of claim 2, wherein the plastic is nylon.

5. A method of making a biocidal article of manufacture, comprising enclosing within a fluid-permeable mesh bag a composition comprising a biocidal agent, wherein the agent is an aldehyde; a carrier admixed with the agent to form a mixture; a film-forming polymer coating around the mixture which is insoluble in a selected solvent; and an activator.

6. The method of claim 5, wherein the activator is and alkalinating agent.

7. The method of claim 6, wherein the alkalinating agent is sodium bicarbonate, borax, disodium hydrogen phosphate, or a mixture thereof.

8. The method of claim 6, wherein the alkalinating agent is sodium bicarbonate.

9. A method of making a biocidal composition, comprising:
   a) admixing a carrier with an aldehyde to form a mixture;
   b) coating the mixture with a film-forming polymer coating which is insoluble in a selected solvent; and
   c) contacting the aldehyde with an acidifying agent before the admixing step, wherein the acidifying agent is acetic acid, hydrochloric acid, phosphoric acid or a mixture thereof.

10. The method of claim 9, wherein the acidifying agent is acetic acid.

11. The method of claim 5, wherein the mesh bag is comprised of a plastic.

12. The method of claim 11, wherein the plastic is a nylon, polyester, polyethylene, polypropylene, fluorocarbon, or a mixture thereof.

13. The method of claim 11, wherein the plastic is nylon.

14. The article of claim 1, wherein the selected solvent is water and the film-forming polymer is a water-insoluble polymer.

15. The method of claim 5, wherein the selected solvent is water and the film-forming polymer is a water-insoluble polymer.

16. A biocidal composition, comprising:

a) a biocidal compound which is liquid at a preselected processing temperature;

b) a carrier admixed with the compound to form a mixture; and c) a film-forming polymer coating around the mixture which is insoluble in a selected solvent, wherein the selected solvent is water and the film-forming polymer is a water-insoluble polymer.

17. A composition, comprising:

a) a compound which is liquid at a preselected processing temperature;

b) a carrier admixed with the compound to form a mixture; and c) a film-forming polymer coating around the mixture which is insoluble in a selected solvent, wherein the selected solvent is water and the film-forming polymer is a water-insoluble polymer.

* * * * *